United States Patent [19]

Ploeg

[11] 3,933,815
[45] Jan. 20, 1976

[54] TRIFLUOROMETHYL TRIAZINES

[75] Inventor: Hermanus L. Ploeg, Wilmington, Del.

[73] Assignee: E. I. Du Pont de Nemours and Company, Wilmington, Del.

[22] Filed: June 24, 1974

[21] Appl. No.: 482,792

[52] U.S. Cl............ 260/248 NS; 260/249.5; 71/93; 260/563 C; 260/453 P; 260/553 R; 260/561 A
[51] Int. Cl.²...................................... C07D 263/46
[58] Field of Search.................. 260/248 NS, 249.5

[56] References Cited
UNITED STATES PATENTS 3,505,057   4/1970   Luckenbaugh ......................... 71/93
3,855,219   12/1974  Fuchs et al. ....................... 260/248

FOREIGN PATENTS OR APPLICATIONS 1,912,224   11/1970   Germany
1,912,226   11/1970   Germany
1,083,752   9/1967    United Kingdom
16,366      12/1971   Sweden Primary Examiner—John M. Ford

[57] ABSTRACT

Herbicidal triazines of the formula

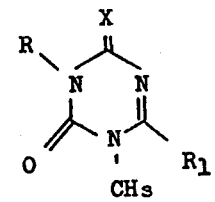

I wherein
R is certain organic radicals containing trifluoromethyl,
$R_1$ is certain organic radicals, and
X is oxygen or sulfur.

Exemplary of such compounds is: 1-methyl-3-(3-trifluoromethylcyclohexyl)-6-dimethylamino-s-triazine-2,4(1H,3H)-dione.

6 Claims, No Drawings

TRIFLUOROMETHYL TRIAZINES

BACKGROUND OF THE INVENTION

Johnson "Pesticides 72," Chemical Week, June 21 and July 26, 1972, lists several commercial and experimental s-triazine herbicides. Among these are atrazine, simazine, prometone, and prometryne:

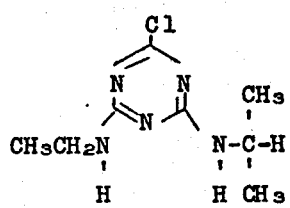

atrazine

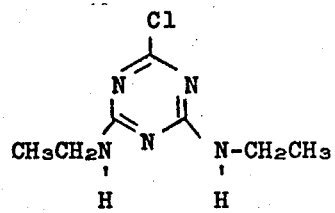

simazine

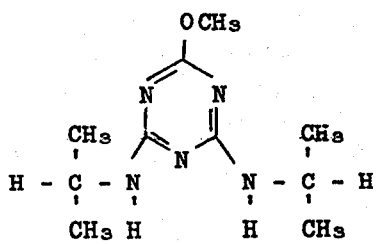

prometone

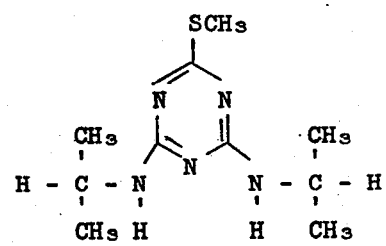

prometryne

Copending U.S. Pat. application Ser. No. 348,321, filed Apr. 5, 1973, now abandoned by Kang Lin (which is a continuation-in-part of U.S. Pat. application Ser. No. 256,249, filed May 24, 1972, now abandoned) discloses a class of s-triazines of the general formula:

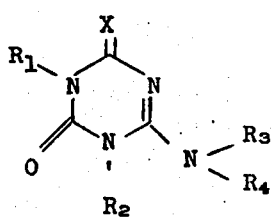

II where
  x is oxygen or sulfur;
  $R_1$ is certain organic radicals including certain cyclic radicals;
  $R_2$ is hydrogen, lower alkyl, or certain cations;
  $R_3$ is hydrogen or certain lower alkyls; and
  $R_4$ is certain organic radicals
These compounds are disclosed as being useful as herbicides.

Copending U.S. Pat. application Ser. No. 348,322, filed Apr. 5, 1973, by Julius Jakob Fuchs and Kang Lin, now U.S. Pat. No. 3,873,540 granted Mar. 25, 1975, (which is a continuation-in-part of U.S. Pat. application Ser. No. 325,358, filed Jan. 22, 1973 now abandoned) discloses a class of s-triazines of the general formula:

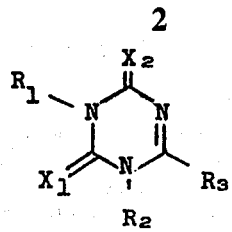

III where
  $X_1$ and $X_2$ are oxygen or sulfur;
  $R_1$ is certain organic radicals including certain cyclic radicals;
  $R_2$ is certain lower alkyl radicals; and
  $R_3$ is $SR_4$ or $OR_4$
    where $R_4$ is certain organic radicals, including certain lower alkyl radicals.

These compounds are disclosed as being useful as herbicides.

The compounds of the present invention result from efforts to develop new herbicidal compounds.

SUMMARY OF THE INVENTION

This invention relates to novel compounds of the following formula and their use as herbicides:

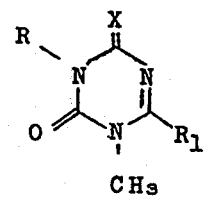

I wherein
R is

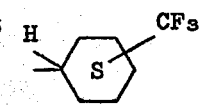 or 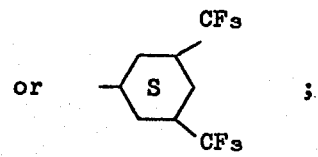 ;

$R_1$ is $-OCH_3$, $-SCH_3$, $-NHCH_3$, or $-N(CH_3)_2$; and

X is oxygen or sulfur.

This invention also includes herbicidal compositions containing the above compounds as active ingredients and methods of controlling undesirable vegetation by applying the compounds and/or compositions.

DESCRIPTION OF THE INVENTION

Preferred Compounds

Certain of the compounds of formula I are preferred because of their higher herbicidal activity. These include those compounds of formula I where:

R is

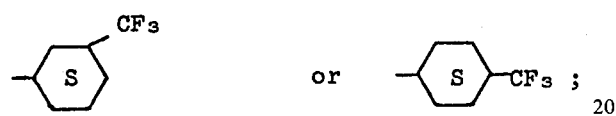

or those compounds of formula I where X is oxygen; or those compounds of formula I where $R_1$ is dimethylamino.

More preferred, of course, are those compounds of formula I satisfying all three of these requirements, namely, those compounds where:

R is

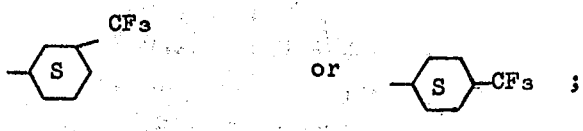

X is oxygen; and $R_1$ is dimethylamino;

i.e., 1-methyl-3-(3-trifluoromethylcyclohexyl)-6-dimethylamino-s-triazine-2,4(1H,3H)-dione, and 1-methyl-3-(4-trifluoromethylcyclohexyl)-6-dimethylamino-s-triazine-2,4(1H,3H)-dione.

In addition, certain compounds are preferred because of both their utility as intermediates for the abovementioned preferred compounds and for their high herbicidal activity. These include:

1-methyl-3-(3-trifluoromethylcyclohexyl)-6-methylthio-s-triazine-2,4(1H,3H)-dione, and 1-methyl-3-(4-trifluoromethylcyclohexyl)-6-methylthio-s-triazine-2,4(1H,3H)-dione.

Synthesis of the Compounds

The compounds of formula I can be made by the process described and exemplified hereinafter. Unless stated otherwise, all percentages are by weight.

A method for preparing the compounds of the present invention is represented schematically in equations (1) through (8) below:

(1) 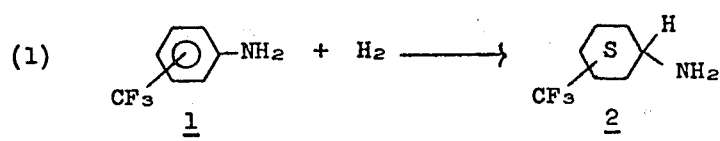

(1a) 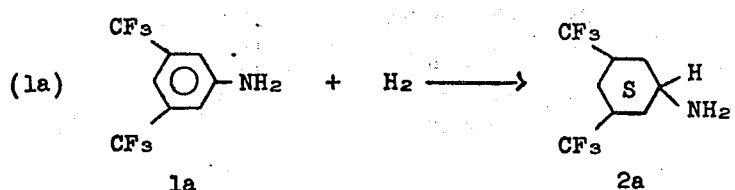

(2) 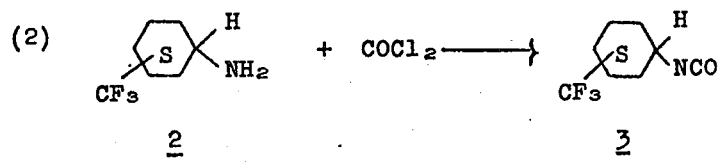

(2a) 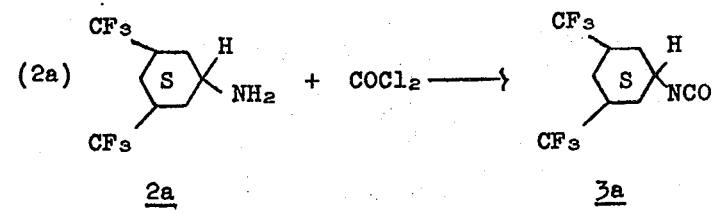

(3) 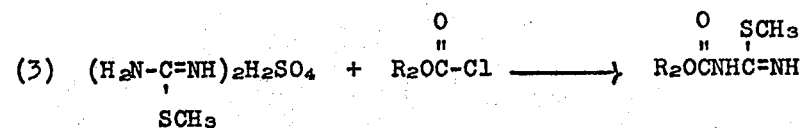

(4) 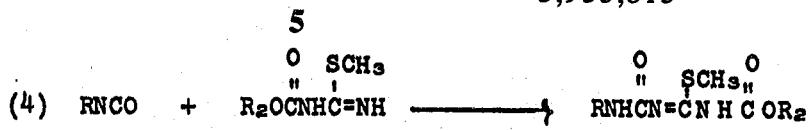
(5) 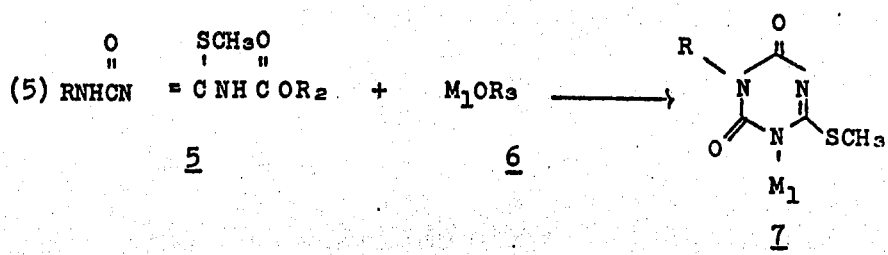
(6) 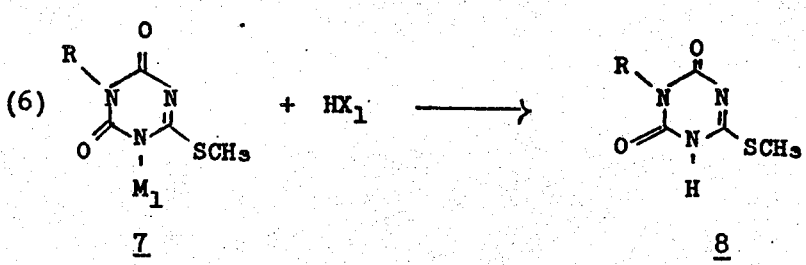
(7) 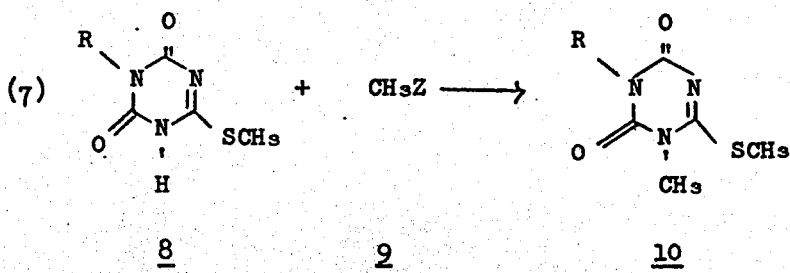
(8a) 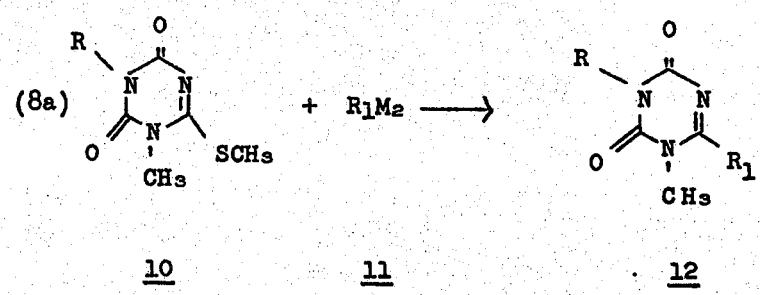
(8b) 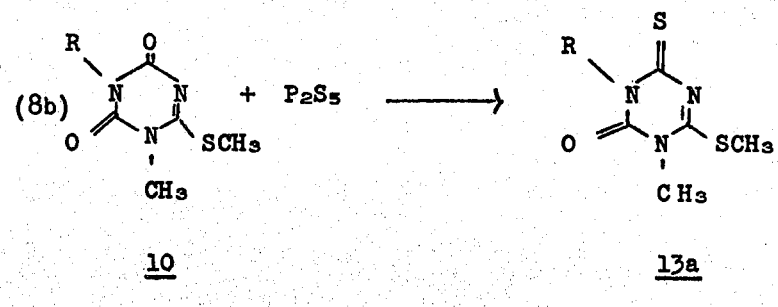

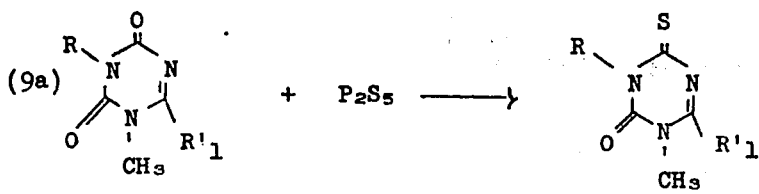

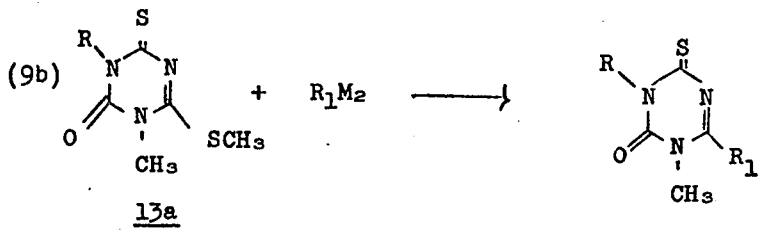

wherein
R, X, and $R_1$ are as previously defined
$R_1'$ is methylthio or dimethylamino;
$R_2$ is alkyl of one through three carbon atoms;
$R_3$ is hydrogen or alkyl of one through four carbon atoms;
$M_1$ is an alkali metal;
$M_2$ is hydrogen when $R_1$ is methylamino and dimethylamino, or $M_2$ is hydrogen or an alkali metal when $R_1$ is methoxy and methylthio;
$X_1$ is chlorine, bromine, iodine, nitrate, or bisulfate; and
Z is iodine or

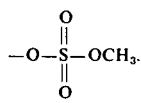

A 10 to 60% solution, preferably 30 to 50%, of compound 1 or 1a in an organic solvent such as ethanol, methanol, or dioxane, preferably dioxane, with 0.01 to 0.1, preferably 0.05 to .075, molecular equivalents of sodium methylate and 0.01 to 0.1, preferably 0.075 to 0.1, weight equivalents of a ruthenium on alumina catalyst containing 1 to 10%, preferably 5%, ruthenium is charged to an autoclave and reacted with hydrogen gas at 100° to 250°C., preferably 165° to 200°C., and most preferably 175°C., and 3,000 to 6,000 p.s.i., preferably 5,000 p.s.i. The reaction is allowed to continue until about one-half hour after the hydrogen pressure has stabilized. This generally occurs in about 2 to 16 hours.

After the reaction has proceeded thus, the reaction mixture is filtered to remove the ruthenium catalyst and the filtrate is evaporated under vacuum to give the appropriate cyclohexylamine 2 or 2a. This intermediate can be used directly for the next reaction or can be purified by distillation.

A solution of compound 2 or 2a in an inert organic solvent is contacted at −40° to 25°C., preferably 0° to 5°C., with 1.0 to 2.5, preferably 1.2 to 1.4, molecular equivalents of phosgene in an inert organic solvent. The organic solvent may be selected from the group consisting of benzene, toluene, xylene, ethyl acetate, and monochlorobenzene; xylene is preferred. The solution of compound 2 or 2a may contain 10 to 40% of compound 2 or 2a, preferably 15 to 25%. The solution of phosgene may contain 10 to 50% of phosgene; 20 to 35% is preferred. If a solvent such as benzene is used, the initial reaction must be run at a temperature above the freezing point of the solvent. It is preferred that the solution of compound 2 or 2a be added to the solution of phosgene and that the desired temperature range be maintained by regulating the rate of addition of said solution of compound 2 or 2a.

After the solutions of compound 2 or 2a and phosgene are contacted, the reaction mixture is heated to 50° to 145°C. or to the boiling point of the solvent being used. for 1 to 15 hours. It is preferred to use xylene as the solvent and to carry out the reaction at 130° to 145°C. for 3 to 5 hours. Higher temperatures permit shorter reaction times.

The progress of the reaction can be measured by the disappearance of compound 2 or 2a and the appearance of compound 3 or 3a as analyzed by gas chromatography and infrared spectroscopy. After the reaction has reached the desired stage of completion, the isocyanate 3 or 3a is isolated by distillation at reduced pressure.

A solution of 2-methyl-2-thiopseudourea sulfate is treated simultaneously with 0.8 to 2.0, preferably 1.0 to 1.2, molecular equivalents of an alkyl chloroformate and 0.8 to 1.8, preferably 1.0 to 1.2 molecular equivalents of a base at 0° to 70°C. The choice of solvents often dictates the preferred reaction temperature; the organic solvents may be selected from benzene, toluene, xylenes, ethyl acetate, monochlorobenzene, chloroform, or methylene chloride and may be used as a co-solvent with water. When water is used as a co-solvent, the reaction temperature should be 0° to 20°C. to prevent excessive reaction of the chloroformate with water. It is preferred to use toluene or methylene chloride as co-solvent with water and to hold the reaction temperature at 5° to 15°C.

The base may be selected from the group consisting of pyridine, triethylamine, sodium hydroxide, and potassium hydroxide in an aqueous or organic solvent; it is preferred to use an aqueous sodium hydroxide solution. For most efficient reaction, the base should be added in such a manner as to maintain the pH of the reaction mass at 8.0 to 10.0, preferably 9.0 to 9.5.

The progress of the reaction can be monitored by gas chromatography; at the conclusion of the reaction the product 4 can be isolated by removal of the organic solvent under reduced pressure followed by crystallization.

Reaction 4 is carried out by contacting a 15 to 50% solution of compound 3 or 3a, preferably 30 to 40% solution, with a 10 to 35% solution of compound 4, preferably 15 to 25%, with or without the addition of a small amount of a basic catalyst selected from the group consisting of pyridine, triethylamine, 1,4-diazabicyclo[2.2.2]octane or dibutyltin dilaurate. It is preferable to use 1 to 4% of 1,4-diazabicyclo[2.2.2]octane on the basis of compound 3 or 3a. The solvent for this reaction may be selected from the group consisting of benzene, toluene, xylenes, methylenechloride, chloroform, and acetonitrile, preferably methylenechloride, toluene, or acetonitrile. The reaction mixture is heated to 40 to 145°C., preferably 60 to 80°C., for 1 to 5 hours, preferably two to three hours. The reaction time is dependent on the nature and amount of solvent in reactants and temperature. The reaction time required for the addition of compound 3 or 3a is not critical and may vary from 0.1 to 10 hours, preferably 0.25 to 1.5 hours. The progress of the reaction can be measured by gas or thin-layer chromatography or by infrared spectroscopy. Compound 5 can be isolated by removal of the solvent under reduced pressure followed by recrystallization or compound 5 can be used in solution for the next reaction. For greater purity it is preferred to isolate and recrystallize compound 5 prior to the subsequent reaction.

A solution of compound 5 in a suitable solvent is treated with an alkali metal alkoxide 6 to give compound 7 which is neutralized with an inorganic acid to give compound 8. The compound 5 is preferably treated with 0.6 to 1.3 equivalents of an alkali metal alkoxide and most preferably with 0.9 to 1.1 equivalents. The alkoxide can be used as a pure base or preferably as a solution in a suitable solvent and most preferably as a 15 to 35% solution in the corresponding alcohol.

The solution of compound 5 can be cyclized to compound 8 by use of an alkali metal hydroxide, but an alcoholic solvent must be added to dissolve the hydroxide before cyclization occurs. Suitable solvents can be selected from the group consisting of alcohols containing one to four carbon atoms, benzene, toluene, xylenes, monochlorobenzene, and nitrobenzene; it is preferred to use sodium methoxide in methanol. The reaction of compound 5 with compound 6 takes place preferably at 25° to 70°C. but most preferably at 45° to 70°C. and requires one to four hours.

The progress of the reaction may be monitored by thin-layer chromatography; at the conclusion of the reaction the solvent may be removed under reduced pressure to give the alkali metal salt 7, which then may either be used directly in the methylation reaction (equation 7) or it can be converted to its free base form, compound 8, by dissolving compound 7 in water and adding 1.0 to 3.0 equivalents of an inorganic acid selected from the group consisting of hydrochloric, hydrobromic, hydroiodic, nitric, and sulfuric acid. The product in this case can be isolated by filtration and drying or can be used directly as a wet solid in the next reaction.

The methylation of compound 8 with methyl iodide or dimethyl sulfate can be carried out in a solvent such as water, acetone, benzene, toluene, xylenes, chlorobenzene, nitrobenzene, acetonitrile, triclene, or perclene.

In the case where dimethyl sulfate is used to alkylate compound 8 the preferred solvent is water because of lower cost and simplicity of product isolation. The product 10 can be isolated by filtration and drying or can be used directly as a wet solid in the next reaction by suspension in an organic solvent and removal of water by azeotropic distillation. When using dimethyl sulfate the pH of the aqueous solution should be maintained between 7 and 11.5, and preferably between 9 and 10.5.

In the case where methyl iodide is the alkylating agent the preferred solvent is acetone and 0.9 to 2.5, preferably 1.0 to 1.5, equivalents of an inorganic base selected from the group consisting of sodium hydroxide, sodium carbonate, potassium carbonate, and potassium hydroxide should be used. The product 10 can be isolated by removal of the solvent under reduced pressure followed by removal of the excess inorganic base and salts by water extraction. The ratio of alkylating agent to compound 8 is preferably from 0.8:1 to 1.5:1, but most preferably 1.1–1.3:1. When an organic solvent is used, the reaction can be carried out at a temperature from 15° to 135°C., preferably 25° to 80°C. When water is the solvent, the temperature range is 15° to 80°C., preferably 25° to 40°C. The progress of the reaction can be visualized by thin-layer chromatography.

The conversion of compound 10 to compound 12 [equation 8(a)] can be carried out in a solvent selected from the group consisting of toluene, xylenes, benzene, monochlorobenzene, triclene, perclene, nitrobenzene, methanol, methylenechloride, and tetrahydrofuran. The preferred solvents are toluene and tetrahydrofuran. The ratio of compound 10 to the amine or methoxide is from 1:1 to 1:6, and preferably, to insure complete conversion to compound 12 and shorter reaction times, 1:2 to 1:3. The reaction of compound 10 can be carried out at temperatures from 5° to 135°C. but preferably from 25° to 60°C. Compound 12 can be isolated by crystallization from the reaction mixture followed by filtration and drying or by removal of the reaction solvent under reduced pressure and recrystallization of the residue.

A method for making those compounds of this invention where X is sulfur is illustrated by equations 8(b), 9(a), and 9(b). Compounds 13a and 13b can be prepared by heating the corresponding oxygen analog 10 or 12a, respectively, with phosphorous pentasulfide at 25° to 150°C. for 1 to 12 hours in a solvent such as pyridine, picoline, or toluene. Pyridine at reflux temperatures is preferred for a faster reaction, while toluene is preferred for ease of product isolation. The products 13a and 13b can be isolated by dilution of the reaction mixture with a suitable hydrocarbon solvent such as toluene, separating the solids and further extraction of the solids with the hydrocarbon solvent followed by crystallization of the product from the hydrocarbon solvent extracts. Alternatively, the reaction mixture can be treated with water and the product extracted and crystallized as above.

Equation 9(b) proceeds as described above with respect to the conversion of compound 10 to compound 12.

The following examples further illustrate this method of synthesis for the compounds of the present invention. All parts are by weight and all temperatures are in degrees centigrade unless otherwise indicated.

EXAMPLE 1

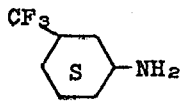

A mixture of 200 parts of 3-aminobenzotrifluoride, 4 parts of sodium methoxide, 15 parts of 5% ruthenium on alumina, and 200 parts of dioxane is heated in an autoclave at 175°C. under 5,000 p.s.i. of hydrogen for 4 hours. The reaction mixture is cooled and filtered and the solvent is evaporated in a rotary evaporator. The residue is distilled to give 159 parts of 3-trifluoromethylcyclohexylamine, b.p. 69°–70°/27 mm.

The following compounds have been prepared similarly.

TABLE I

| Compounds | Boiling Point | Yield |
|---|---|---|
| $\begin{array}{c}\text{CF}_3\\ \langle S \rangle\text{—NH}_2\end{array}$ | 50–52°C/23mm | 64% |
| $CF_3\text{—}\langle S \rangle\text{—NH}_2$ | 67–71°C/28mm | 69% |
| $\begin{array}{c}CF_3\\ \langle S \rangle\text{—NH}_2\\ CF_3\end{array}$ | 76°C/13mm | |

EXAMPLE 2

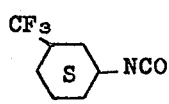

To a stirred solution of 130 parts of phosgene in 450 parts of xylene at 0° to 5°C. is added dropwise a solution of 100 parts of 3-trifluoromethylcyclohexylamine (prepared as in Example 1) in 450 parts of xylene. The reaction mixture is stirred at 0°C. for 1 hour, allowed to come to ambient temperature, and then refluxed 4 hours. The excess phosgene is trapped in a gas scrubber. The xylene is stripped on a rotary evaporator and the residue is distilled under reduced pressure to yield 62.4 parts of 3-trifluoromethylcyclohexyl isocyanate, b.p. 68°–69°C/9mm.

The following compounds have been prepared similarly:

TABLE II

| Compounds | Boiling Point | Yield |
|---|---|---|
| $\begin{array}{c}\text{CF}_3\\ \langle S \rangle\text{—NCO}\end{array}$ | 91–93°C/22mm | 42% |
| $CF_3\text{—}\langle S \rangle\text{—NCO}$ | 83–85°C/14mm | 48% |
| $\begin{array}{c}CF_3\\ \langle S \rangle\text{—NCO}\\ CF_3\end{array}$ | 76°C/13mm | |

EXAMPLE 3

At 10°C. 417 parts of 2-methyl-2-thiopseudourea sulfate is dissolved in a mixture of 1,250 parts of water and 1,335 parts of methylene chloride. While maintaining the temperature at 10°C. and pH at 9.0 to 9.5, 282 parts of methyl chloroformate and 480 parts of 50% sodium hydroxide solution are simultaneously added dropwise over 1½ hours. The methylene chloride layer is separated, dried with magnesium sulfate, and evaporated on a rotary evaporator. The residue was recrystallized from carbon tetrachloride to yield 355 parts of the subject compound, m.p. 76°–78°C.

EXAMPLE 4

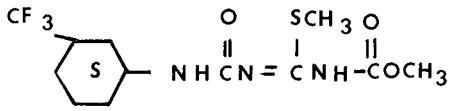

To a solution of 14.6 parts of

(produced by the process of Example 3) in 80 parts of acetonitrile containing 0.25 parts of 1,4-diazabicyclo[2.2.2]octane is added dropwise a solution of 19.3 parts of 3-trifluoromethylcyclohexyl isocyanate in 40 parts of acetonitrile. The solution is refluxed for 3 hours and the solvent is stripped in a rotary evaporator. The residue is recrystallized from 1-chlorobutane to yield 28.4 parts of the subject compound, m.p. 108°–111°C.

The following compounds have been prepared similarly.

TABLE III

| Compound | Properties | Yield |
|---|---|---|
| [CF3-thiophene-NHCN=C(SCH3)NH-COCH3 with two C=O] | Waxy Solid | 79% |
| [CF3-thiophene-NHCN=C(SCH3)NH-COCH3] | m.p. 95–99°C. | 85% |
| [bis-CF3-thiophene-NHCN=C(SCH3)NH-COCH3] | m.p. 170–173°C. | |

EXAMPLE 5

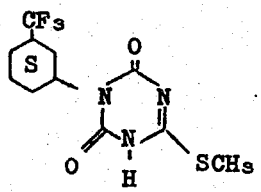

A solution of 35.2 parts of the compound produced by Example 4, 6 parts of sodium methoxide and 700 parts of methanol is refluxed for 1 hour. The methanol is stripped on a rotary evaporator and the residue is dissolved in 100 parts of water. The aqueous solution is neutralized with hydrochloric acid. The solid is filtered off and dried to yield 28 parts of the subject compound, m.p. 176°–180°C.

The following compounds can be prepared similarly.

TABLE IV

| Compound | Melting Point |
|---|---|
| [CF3-thiophene-triazine-SCH3, NH] | |
| [CF3-cyclohexyl-S-triazine-SCH3, NH] | 273–274.5°C. |

TABLE IV-continued

| Compound | Melting Point |
|---|---|
| [bis-CF3-thiophene-triazine-SCH3, NH] | |

EXAMPLE 6

[CF3-thiophene-triazine with SCH3 and N-CH3]

A mixture of 28 parts of the compound produced by the process of Example 5, 20 parts of powdered potassium carbonate, 30 parts of methyl iodide, and 200 parts of acetone is refluxed overnight. The solvent is evaporated and the residue is dissolved in 260 parts of methylene chloride. The methylene chloride solution is washed with water, dried with magnesium sulfate, and evaporated to afford 23 parts of the subject compound as a soft solid.

The following compounds can be prepared similarly.

TABLE V

| Compound | Properties |
|---|---|
| [CF3-thiophene-triazine-SCH3, N-CH3] | soft solid |
| [CF3-cyclohexyl-S-triazine-SCH3, N-CH3] | soft solid |
| [bis-CF3-thiophene-triazine-SCH3, N-CH3] | m.p. 126–130°C. |

EXAMPLE 7

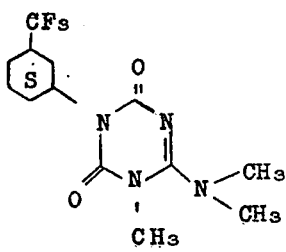

A solution of 12.4 parts of a compound produced by the process of Example 6 in 45 parts of tetrahydrofuran at 0°C. is treated with 7 parts of anhydrous dimethylamine. The reaction mass is allowed to warm to room temperature and stand overnight. The solvent is stripped on a rotary evaporator and the semi-solid residue triturated with a small amount of hexane to afford 10.2 parts of the subject compound, m.p. 110°–112°C.

EXAMPLE 8

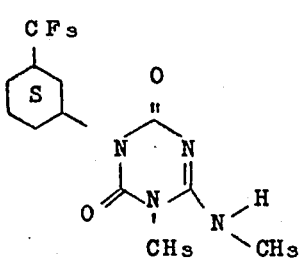

A solution of 8.5 parts of the compound produced by the process of Example 6 in 45 parts of tetrahydrofuran is treated with 15 parts of 40% aqueous methylamine. The reaction mass is stirred overnight and then filtered to yield, after drying, 9.8 parts of the subject compound, m.p. 234°–236°C.

EXAMPLE 9

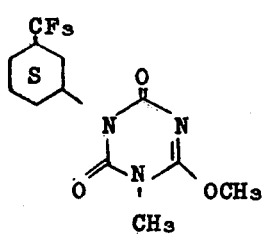

A solution of 10.7 parts of the compound produced by the process of Example 6 and 2.0 parts of sodium methoxide in 79 parts of methanol is refluxed overnight. The solvent is removed on a rotary evaporator and the residue dissolved in methylene chloride. The methylene chloride solution is washed with water, dried with magnesium sulfate, and evaporated to give the subject compound.

The following triazines can be prepared by procedures analogous to those in Examples 7, 8, and 9 above:

TABLE VI

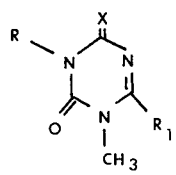

| R | $R_1$ | X |
|---|---|---|
| 3-CF₃-thiophenyl (cyclohexyl-S) | —NHCH₃ | O |
| 3-CF₃-thiophenyl | —NHCH₃ | S |
| 3-CF₃-thiophenyl | —N(CH₃)₂ | O |
| 3-CF₃-thiophenyl | —N(CH₃)₂ | S |
| 3-CF₃-thiophenyl | —OCH₃ | O |
| 3-CF₃-thiophenyl | —OCH₃ | S |
| 2-CF₃-thiophenyl | —NHCH₃ | S |
| 2-CF₃-thiophenyl | —N(CH₃)₂ | S |
| 2-CF₃-thiophenyl | —OCH₃ | S |
| 2-CF₃-thiophenyl | —NHCH₃ | O |

TABLE VI-continued

R, R₁, X columns with structure shown:

| R | R₁ | X |
|---|---|---|
| 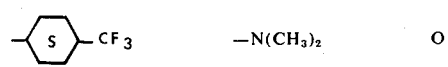 4-CF₃-thiophenyl | —NHCH₃ | S |
| 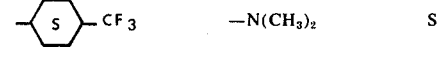 4-CF₃-thiophenyl | —N(CH₃)₂ | O |
| 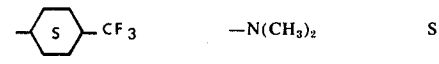 4-CF₃-thiophenyl | —N(CH₃)₂ | S |
|  4-CF₃-thiophenyl | —OCH₃ | O |
| 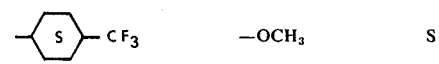 4-CF₃-thiophenyl | —OCH₃ | S |
|  di-CF₃-thiophenyl | NHCH₃ | O |
|  di-CF₃-thiophenyl | N(CH₃)₂ | O |
|  di-CF₃-thiophenyl | OCH₃ | O |

EXAMPLE 10

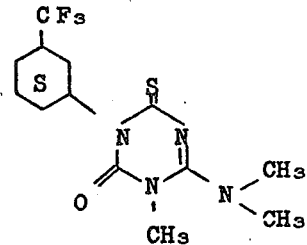

To 20 parts of the compound produced by the process of Example 7 in 200 parts of pyridine is added 40 parts of phosphorous pentasulfide. The mixture is refluxed for 6 hours under a nitrogen atmosphere. The hot reaction mixture is diluted with 250 parts of toluene and the supernatant liquid decanted. The residue is washed twice with 200 parts each of hot toluene and the supernatant liquid decanted. The combined supernatant portions are concentrated to dryness and extracted with hot toluene. The hot extract is filtered then cooled to give the subject compound.

The following 4-thiotriazines can be prepared similarly.

TABLE VII

| R | R₁ |
|---|---|
| di-CF₃-thiophenyl | —N(CH₃)₂ |
| di-CF₃-thiophenyl | —SCH₃ |
| di-CF₃-thiophenyl | —SCH₃ |
| 4-CF₃-thiophenyl | —N(CH₃)₂ |
| 4-CF₃-thiophenyl | —SCH₃ |

TABLE VII-continued

[Structure: 1,3,5-triazine ring with R-N, C=S, N-CH3, N, C-R1, N-C=O]

| R | R1 |
|---|---|
| [thiophene with two CF3 groups] | —N(CH$_3$)$_2$ |
| [thiophene with two CF3 groups] | —SCH$_3$ |
| [thiophene with two CF3 groups] | —NHCH$_3$ |
| [thiophene with two CF3 groups] | —OCH$_3$ |

FORMULATIONS OF THE COMPOUNDS

Useful formulations of the compounds of formula I can be prepared in conventional ways. They include dusts, granules, pellets, solutions, suspensions, emulsions, wettable powders, emulsifiable concentrates, and the like. Many of these can be applied directly. Sprayable formulations can be extended in suitable media and used at spray volumes of from a few pints to several hundred gallons per acre. High strength compositions are primarily used as intermediates for further formulation. Broadly speaking, these formulations consist essentially of about 1% to 99% by weight of herbicidally active material (including at least one compound of formula I in an herbicidally effective amount) and at least one of (a) about 0.1% to 20% surfactant(s) and (b) about 5% to 99% solid or liquid diluent(s). More specifically, they will contain these ingredients in the following approximate proportions:

|  | Percent by Weight | | |
|---|---|---|---|
|  | Herbicide | Diluent | Surfactant |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical and chemical properties of the compound. Higher ratios of surfactant to active ingredient are sometimes desirable and are achieved by incorporation into the formulation or by tank mixing.

Typical solid diluents are described in Watkins et al., *Handbook of Insecticide Dust Diluents and Carriers*, 2nd Edition, Dorland Books, Caldwell, N.J. The more absorptive diluents are preferred for wettable powders and the denser ones for dust. Typical liquid diluents and solvents are described in Marsden, "Solvents Guide," 2nd Edition, Interscience, N.Y., 1950. Solubility under 0.1% is preferred for suspension concentrates; solution concentrates are preferably stable against phase separation at 0°C. "McCutcheon's Detergents and Emulsifiers Annual," Allured Publ. Corp., Ridgewood, N.J. as well as Sisely and Wood, Encyclopedia of Surface Active Agents, Chemical Publ. Co., Inc., N.Y., 1964, lists surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and usually grinding as in a hammer or fluid energy mill. Suspensions are prepared by wet milling (see, for example, Littler, U.S. Pat. No. 3,060,084). Granules and pellets can be made by spraying the active material upon pre-formed granular carriers or by agglomeration techniques. (See, J. E. Browning, "Agglomeration," Chemical Engineering, December 4, 1967, pages 147ff. and Perry's Chemical Engineers' Handbook, 4th Edition, McGraw-Hill, N.Y., 1963, pages 8 through 59ff.)

For further information regarding the art of formulations, see, for example:

H. M. Loux, U.S. Pat. No. 3,253,361, Feb. 15, 1966, column 6, line 16 through column 7, line 19, R. W. Luckenbaugh, U.S. Pat. No. 3,309,192, Mar. 14, 1967, column 5, line 43 through column 7, line 62, and examples 8, 12, 15, 39, 41, 52, 53, 58, 132, 138 through 140, 162 through 164, 166, 167, 169 through 182.

H. Gysin and E. Knusli, U.S. Pat. No. 2,891,855, June 23, 1959, column 3, line 66 through column 5, line 17, and examples 1 through 4.

G. C. Klingman, *Weed Control as a Science*, John Wiley and Sons, N.Y., 1961, pages 81 to 96.

J. D. Frier and S. A. Evans, *Weed Control Handbook*, 5th Edition, Blackwell Scientific Publications, Oxford, 1968, pages 101–103.

Typical formulations are shown in the following examples:

EXAMPLE 11

| Wettable Powder | Percent |
| --- | --- |
| 1-methyl-3-(3-trifluorocyclohexyl)-6-dimethyl-amino-s-triazine-2,4(1H,3H)-dione | 40% |
| dioctylsodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill to produce an average particle size under 15 microns, reblended, and sifted through a U.S.S. No. 50 sieve (0.3mm opening) before packaging.

All compounds of the invention can be formulated in the same manner.

EXAMPLE 12

| Extruded Pellet | Percent |
| --- | --- |
| 1-methyl-3-(4-trifluoromethylcyclohexyl)-6-dimethylamino-s-triazine-2,4(1H,3H)-dione | 25% |
| anhydrous sodium sulfate | 10% |
| crude calcium ligninsulfonate | 5% |
| sodium alkylnaphthylenesulfonate | 1% |
| calcium/magnesium bentonite | 59% |

The ingredients are blended, hammer milled, and then moistened with about 12% water. The mixture is extruded as cylinders about 3mm diameter which are cut to produce pellets about 3mm long. These may be used directly after drying or the dried pellets may be crushed to pass a U.S.S. No. 20 sieve (0.84mm openings). The granules held on a U.S.S. No. 40 sieve (0.42mm openings) may be packaged for use and the fines recycled.

EXAMPLE 13

| Aqueous Suspension | Percent |
| --- | --- |
| 1-methyl-3-(3-trifluoromethylcyclohexyl)-6-methyl-thio-s-triazine-2,4(1H,3H)-dione | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 14

| Emulsifiable Concentrate | Percent |
| --- | --- |
| 1-methyl-3-(2-trifluoromethylcyclohexyl)-6-dimethyl-amino-s-triazine-2,4(1H,3H)-dione | 25.0% |
| isophorone | 67.0% |
| blend of oil-soluble sulfonates with polyoxyethylene ethers | 8.0% |

The above ingredients are mixed in a blender until a homogeneous emulsifiable solution results.

EXAMPLE 15

| High Strength Composition | Percent |
| --- | --- |
| 1-methyl-3-(4-trifluoromethylcyclohexyl)-6-methyl-amino-s-triazine-2,4(1H,3H)-dione | 90.0% |
| hydrous sodium silicoaluminate | 8.5% |
| methylated cellulose | 0.5% |
| dioctylsodium sulfosuccinate | 1.0% |

The above ingredients are blended, hammer milled to pass a 0.30mm screen and reblended. The resulting high strength composition is suitable for direct application or it can be used for further formulation.

USE OF THE COMPOUNDS

The compounds of formula I are useful for the control of undesired vegetation. They can be used wherever weed control is required, such as on industrial sites, railroad rights-of-way, and locations adjacent to crop lands.

The precise amount of the compounds of formula I to be used in any given situation will vary according to the particular end result desired, the use involved, the plant and soil involved, the formulation used, the mode of application, prevailing weather conditions, foliage density, and like factors. Since so many variables play a role, it is not possible to state a rate of application suitable for all situations. Broadly speaking, the compounds of the invention are used at levels of about 1 to about 25 kilograms per hectare. The lower rates in this range will generally be selected on lighter soils, soils low in organic matter content, or in situations where maximum persistence is not necessary.

The compounds of formula I can be combined with any other herbicide and they are particularly useful in combination with herbicides of the substituted urea, uracil, or s-triazine types for controlling a broad spectrum of weeds.

The herbicidal activity of the compounds of this invention is demonstrated by the following greenhouse tests:

Seeds of crabgrass (Digitaria spp.), barnyardgrass (Echinochloa spp.), wild oats (*Avena fatua*), *Cassia tora*, moringglory (Ipomoea spp.), cocklebur (Xanthium spp.), and nutsedge (*Cyperus rotundus*) tubers were planted in a growth medium and treated pre-emergence with the chemicals dissolved in a nonphytotoxic solvent. At the same time, crabgrass with two leaves, barnyardgrass with two leaves, wild oats with one leaf, Cassia with three leaves (including cotyledonary leaves), moringglory with four leaves (including cotyledonary leaves), cocklebur with four leaves (including cotyledonary leaves), and nutsedge with three to five leaves were sprayed. Treated plants and controls were maintained in a greenhouse for 16 days. Then all species were compared to controls and visually rated for response to treatment. A quantitative rating was made on the scale of 0 to 10; a rating of 10 means complete kill, a rating of 0 means no injury. A qualitative rating for type of injury was also made. The letter "C" indicates chlorosis/necrosis. Ratings in this test for several of the compounds of formula I are shown in the following table:

|  | | POST-EMERGENCE | | | | | | | PRE-EMERGENCE | | | | | | |
|---|---|---|---|---|---|---|---|---|---|---|---|---|---|---|---|
| Compound | KG/HA | A | B | C | D | E | F | G | A | B | C | D | E | F | G |
| Structure 1 (1-methyl-3-(3-trifluoromethylcyclohexyl)-6-dimethylamino-s-triazine-2,4(1H,3H)-dione) | 2 | 10C | 10C | 10C | 5C | 10C | 10C | 10C | 10C | 10C | 0C | 0 | 8C | 10C | 9C |
| Structure 2 | 0.4 | 10C | 10C | 10C | 4C | 10C | 10C | 10C | 10C | 3C | 0C | 0 | 8C | 10C | 9C |
| Structure 3 | 2 | 10C | 10C | 10C | 9C | 10C | 10C | 10C | 10C | 5C | 0C | 0 | 9C | 10C | 9C |

A = Morningglory
B = Cocklebur
C = Cassia
D = Nutsedge
E = Crabgrass
F = Barnyardgrass
G = Wild Oats

What is claimed is:

1. A compound of the formule where R is $H-\text{(cyclohexyl)}-CF_3$ or $-\text{(cyclohexyl)}(CF_3)$ ;

$R_1$ is $-OCH_3$, $-SCH_3$, $-NHCH_3$, or $-N(CH_3)_2$; and
X is oxygen or sulfur.

2. A compound of claim 1 wherein R is $-\text{(cyclohexyl)}-CF_3$ or $-\text{(cyclohexyl)}-CF_3$ ;

X is oxygen; and
$R_1$ is dimethylamino.

3. The compound of claim 2 which is 1-methyl-3-(3-trifluoromethylcyclohexyl)-6-dimethylamino-s-triazine-2,4(1H,3H)-dione.

4. The compound of claim 2 which is 1-methyl-3-(4-trifluoromethylcyclohexyl)-6-dimethylamino-s-triazine-2,4(1H,3H)-dione.

5. The compound of claim 1 which is 1-methyl-3-(3-trifluoromethylcyclohexyl)-6-methylthio-s-triazine-2,4-(1H,3H)-dione.

6. The compound of claim 1 which is 1-methyl-3-(4-trifluoromethylcyclohexyl)-6-methylthio-s-triazine-2,4-(1H,3H)-dione.

* * * * *